United States Patent [19]

Matsumoto

[11] Patent Number: 4,653,000
[45] Date of Patent: Mar. 24, 1987

[54] IMAGE SIGNAL-PROCESSING SYSTEM BASED ON SYNTHETIC APERTURE TECHNIQUE

[75] Inventor: Kenzo Matsumoto, Tokyo, Japan

[73] Assignee: Kabushiki Kaisha Toshiba, Kawasaki, Japan

[21] Appl. No.: 646,156

[22] Filed: Aug. 31, 1984

[30] Foreign Application Priority Data

Sep. 6, 1983 [JP] Japan ................................ 58-163666
Sep. 6, 1983 [JP] Japan ................................ 58-163667

[51] Int. Cl.⁴ .................... G06F 15/42; G06G 7/60
[52] U.S. Cl. ................................ 364/414; 364/417;
  73/602; 73/603; 73/625; 128/660
[58] Field of Search ................ 364/414, 417; 128/660;
  73/656, 602, 603, 625

[56] References Cited

U.S. PATENT DOCUMENTS

| Re. 30,443 | 12/1980 | Niklas ................................ 73/602 |
| 3,548,642 | 12/1970 | Flaherty et al. ..................... 73/602 |
| 3,856,985 | 12/1974 | Yokoi et al. ........................ 128/660 |
| 3,942,150 | 3/1976 | Booth ................................ 340/5 H |
| 4,165,647 | 8/1979 | Collins .............................. 73/603 |
| 4,252,024 | 2/1981 | Hurwitz ............................. 73/603 |
| 4,275,595 | 6/1981 | Hassler ............................. 73/606 |

Primary Examiner—E. A. Goldberg
Assistant Examiner—Lincoln D. Donovan
Attorney, Agent, or Firm—Oblon, Fisher, Spivak, McClelland & Maier

[57] ABSTRACT

In an ultrasonic computed tomography system including an image signal-processing apparatus for reconstructing an image signal of an object on the basis of a synthetic aperture technique, a probe includes a transducer unit. The transducer unit emits an ultrasonic beam to the object and detects the corresponding echo wave. Hologram data is produced in response to the echo wave and then digitized to have a predetermined number of bits by A/D converters. The digital hologram data is temporarily stored in buffer memories and read out under the control of a computer unit. The computer unit has a ROM assembled therein to prestore digital kernel function data, the number of whose bits is smaller than that of the digital hologram signals. The computer unit executes a convolution on the digital hologram data and the kernel function data, thus increasing the speed of a computation needed for image reconstruction.

6 Claims, 5 Drawing Figures

F I G. 2
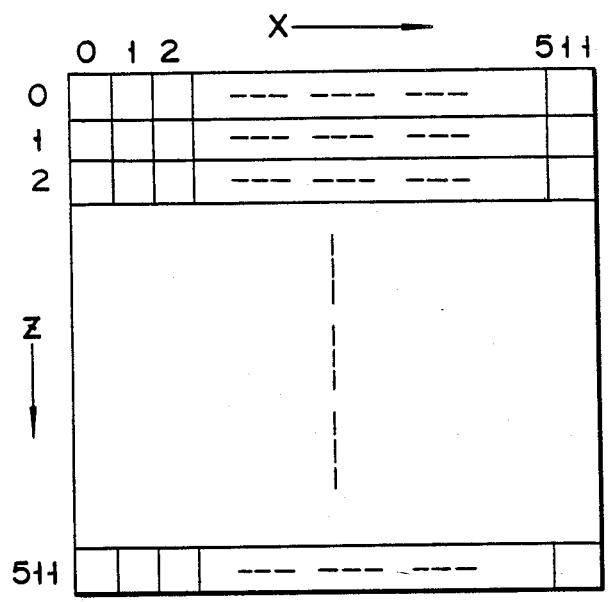

F I G. 3B
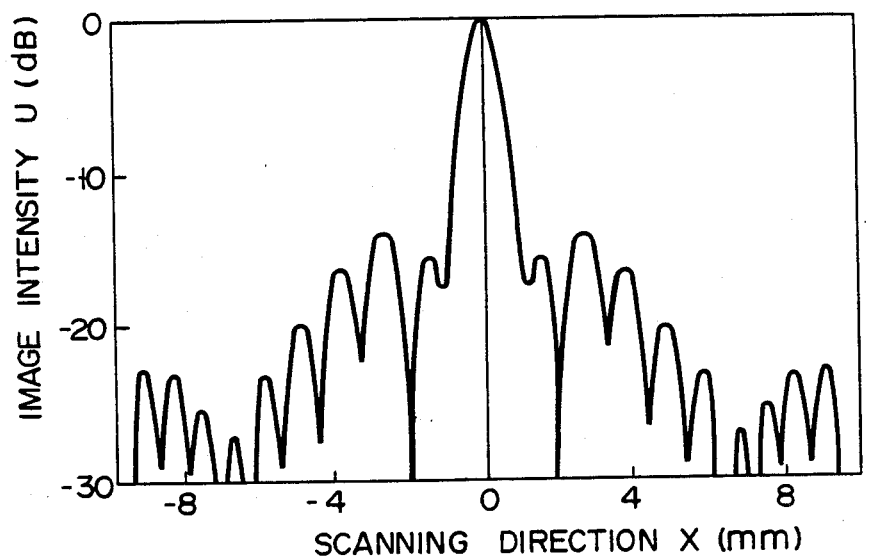

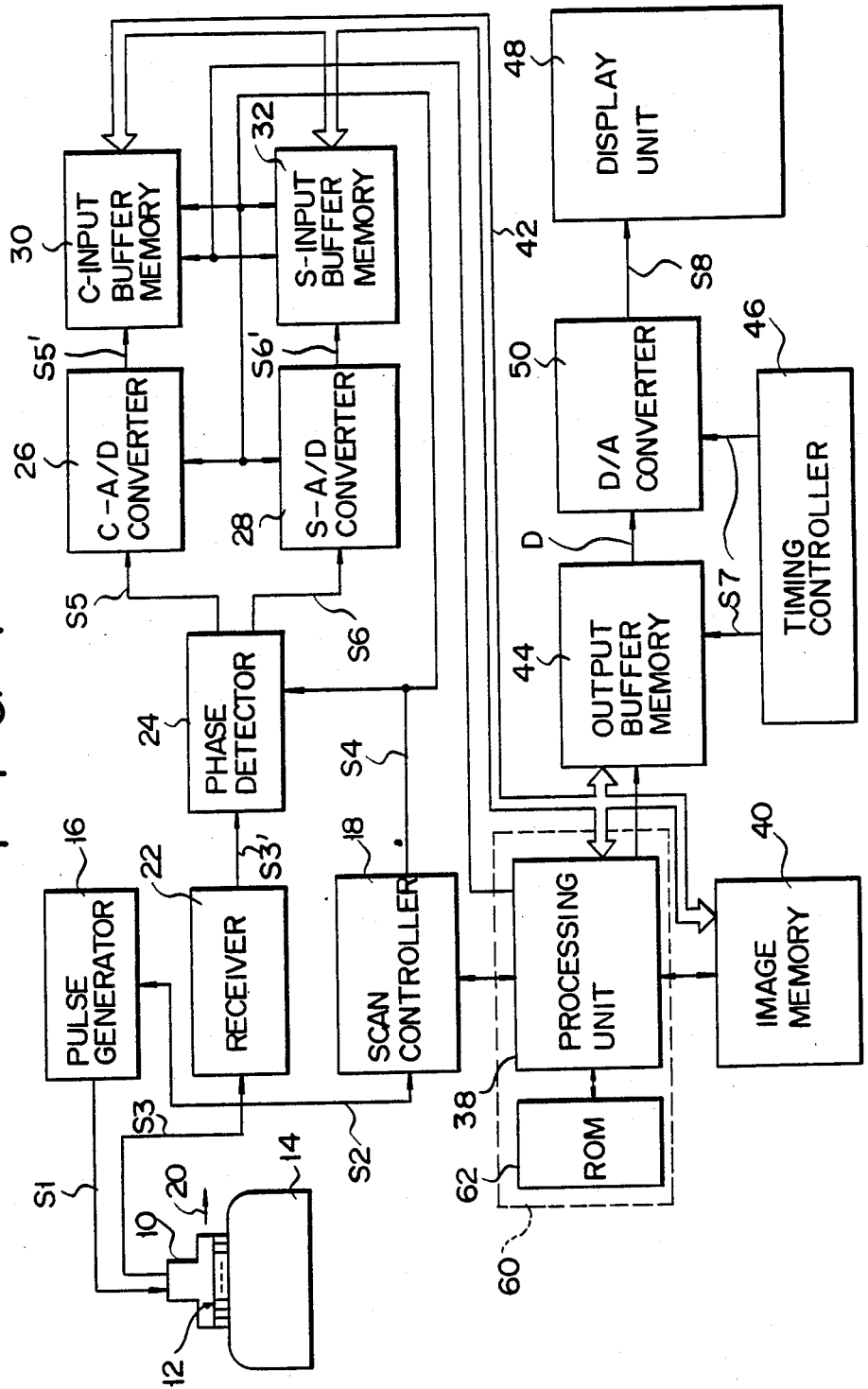

IMAGE SIGNAL-PROCESSING SYSTEM BASED ON SYNTHETIC APERTURE TECHNIQUE

BACKGROUND OF THE INVENTION

The present invention relates in general to an image signal-processing apparatus based on a synthetic aperture technique, and more particularly, to an imaging apparatus which is applied to a synthetic aperture radar or an imaging system effecting the reconstruction of an acoustic image by the synthetic aperture technique.

An image signal-processing apparatus, which applies preferably to a radar or an acoustic imaging system and employs the synthetic aperture technique, emits an electromagnetic beam or an acoustic beam to an object to be detected so that the beam is irradiated with a predetermined angle and detects an image of the object based on a reflected beam from the object. Such a signal-processing apparatus has a nearly constant resolution irrespective of how far a to-be-detected area lies in the object. For this property, the signal-processing apparatus is one of the most effective apparatus in the concerned field.

For example, an imaging system using an ultrasonic beam includes a transducer which emits an ultrasonic beam that is irradiated in the vertical direction. When a to-be-detected object (regarded as a point reflector for easier explanation) is spaced vertically from the beam-emitting end of the transducer, the point reflector is horizontally scanned with the ultrasonic beam. The transducer receives an echo wave from the point reflector and transcribes it into an electrical signal which is supplied to a phase detector. The phase detector subjects the electrical signal to phase detection processing to provide analog hologram signals, which are digitized and stored in corresponding buffer memories.

The reconstruction of the image of the point reflector is carried out by the convolution integration of hologram data and the respective data of a kernel function. Actually, since the hologram data are horizontally digitized, the integration is performed by repeating a phenomenal number of multiplications and additions. Conventional imaging systems require much more time to perform the convolution integration, thus preventing faster image reconstruction.

SUMMARY OF THE INVENTION

It is therefore an object of the present invention to provide a new and improved image signal-processing apparatus, which is able to reconstruct the image of an object at a higher speed.

It is another object of the present invention to provide a new and improved image signal-processing apparatus, which is able to reconstruct the image of an object at a higher speed without substantially impairing the resolution.

A signal-processing apparatus of the present object on the bases of the synthetic aperture technique, includes a transducer unit. The transducer unit emits radiation to the object and detects the corresponding echo wave reflected from the object. The echo wave is converted into an electrical signal, which is transferred to a hologram generator unit. The hologram generator unit generates hologram data representing at least one hologram signal in response to the electrical signal. The hologram signal is converted into digital data of a predetermined number of bits. The digital hologram data is supplied to a computer unit, which prestores digitized kernel function data having a predetermined number of bits smaller than that of the hologram data. The computer unit subjects the digital hologram data and the digital kernel function data to a predetermined arithmetic operation, such as convolution, based on the synthetic aperture technique.

The use of the digital kernel function data with fewer bits speeds up the image reconstruction operation. The experiments conducted by the inventor prove that the resolution and the maximun side lobe level of the image reconstructed according to the present invention is substantially identical with that of the reconstructed image which is attained by using digital kernel function data with larger bits.

BRIEF DESCRIPTION OF THE DRAWINGS

The present invention is best understood with reference to the accompanying drawings, in which:

FIG. 2 is a diagram showing a memory map of an image memory included in the image signal-processing apparatus of FIG. 1;

FIG. 3B is a graph illustrating a waveform of a reconstructed image of a point reflector obtained according to an arithmetic operation of the present invention, which uses a kernel function digitized so as to have bits less than those of hologram data; and FIG. 4 is a block diagram showing the overall arrangement of an ultrasonic computed tomograph system including an image signal-processing apparatus according to another embodiment of the present invention.

DETAILED DESCRIPTION OF THE PREFERRED EMBODIMENTS

Figure 1:
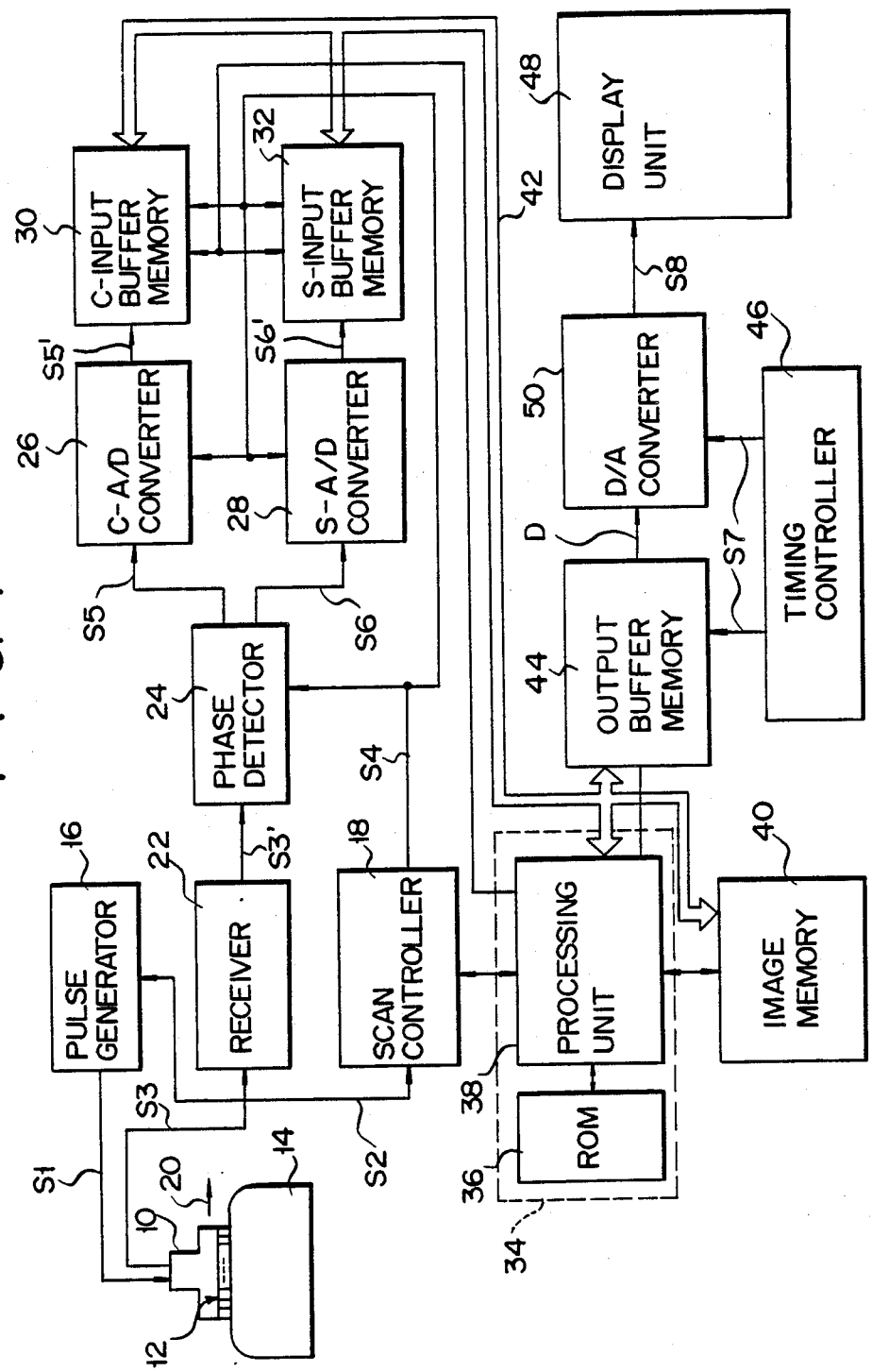
FIG. 1 is a block diagram showing the overall arrangement of an ultrasonic computed tomography system including an image signal-processing apparatus according to one embodiment of the present invention.

FIG. 1 illustrates an ultrasonic diagnostic apparatus or ultrasonic computed tomograph system to which an image signal-processing apparatus embodying the present invention is applied. An ultrasonic probe 10 has an array type transducer unit 12 comprising a plurality of transducer elements. Each transducer element irradiates an ultrasonic beam which spreads with a given angle towards an object 14, in this case, a living body such as a human body. Echo waves from the interior of the living body 14 are received by the respective transducers which have irradiated the corresponding ultrasonic beams. The echo waves are then converted into electrical signals. In this embodiment, a resonance frequency fr of the transducers 12 is preferably selected to be within 2 to 10 MHz.

A pulse generator 16 sequentially supplies a drive pulse signal S1 to those transducers which are specified by a scan controller 18 in synchronism with a control pulse signal S2 from the scan controller 18, thereby driving the transducers. This arrangement enables the transducers 12 to irradiate ultrasonic beams toward the living body 14 at regular intervals, thus scanning the living body 14 in the direction of an arrow 20 which substantially corresponds to the X direction of an X-Z plane.

An electrical detection signal S3 corresponding to the echo wave received by the corresponding transducer 12 of the probe 10 is supplied to a receiver 22, which amplifies the signal S3 to a necessary signal level. A phase detector 24 is provided at the rear stage of the receiver 22 to receive the amplified signal from the receiver 22 and a signal S4, having two types of sinusoidal waveforms, from the scan controller 18. (The frequency of the sinusoidal signal S4 coincides with the resonance frequency fr of the transducers 12.) The phase detector 24 calculates a product of the amplified signal and signal S4 for a phase detection. The phase detector 24 then respectively supplies two hologram signals, a cos hologram signal S5 and a sin hologram signal S6, to first and second analog-to-digital (A/D) converters 26 and 28, which are provided at the rear stage of the phase detector. (These converters are hereafter respectively called C-A/D converter and S-A/D converter in association with the cos and sin hologram signals received thereby.) The C-A/D and S-A/D converters 26, 28 respectively scan the signals S5 and S6 and digitize them into, for example, 8-bit signals to generate digital hologram signals S5' and S6'. The determination of a sampling pitch is based on the duration time of pulsed ultrasound transmitted. For example, when the duration time is 2 $\mu$sec, the sampling pitch is 400 $\mu$sec, 1/5 of the duration time. A sampling clock component included in the signal S4 from the scan controller 18 is an important parameter in deciding the sampling pitch. The C-A/D and S-A/D converters 26, 28 perform the sampling and A/D conversion in synchronism with the sampling clock.

The 8-bit digital hologram signals S5' and S6' are respectively supplied to first and second buffer memories 30 and 32 (hereafter called C- and S-input buffer memories) for storage. The data writing in these buffer memories is also carried out in synchronism with the sampling clock supplied thereto from the scan controller 18. That is, the hologram signals S5' and S6', which are both put through the sampling process, are respectively stored in the buffer memories 30 and 32 in synchronism with the sampling clock. Each of the input buffer memories has a memory capacity sufficient for storing a sequence of echo signals, which is obtained by a single ultrasonic pulse irradiated from one of the transuducers 12. The hologram data once stored in the input buffer memories 30 and 32 is allowed to be read out therefrom under the control of a computer 34 that is connected to the buffer memories 30 and 32 through a data bus 42.

The computer 34 has a ROM (Read Only Memory) 36 and a processing unit 38 assembled therein. The ROM 36 prestores kernel function data based on the synthetic aperture technique, and the processing unit 38 executes the necessary convolution for image reconstruction. The kernel function data is quantized to have a prescribed number of bits.

Careful attention should be paid to the fact that the number of bits of the binary-coded kernel function data (4 bits in this embodiment) is smaller than that of the binary-coded hologram signal (8 bits in this embodiment). The computer 34 is also connected to an image memory 40, which is able to store image data corresponding to a predetermined number of images, e.g., two images. Accordingly, the image memory 40 can at one time store two types of data, cos and sin hologram data (both binary-coded), which have been read out from the input buffer memories 30 and 32 through the data bus 42 under the control of the computer 34. FIG. 2 illustrates the data map defined by the X-Z coordinates in the image memory 40. Both an X-address and a Z-address in the image memory 40 range from 0 to 511. In the image memory 40, the direction X corresponds to the scanning direction of the ultrasonic probe 10 while the direction Z corresponds to the depth direction of the object 14. Each memory address can store a single 8-bit data.

An output buffer memory 44 is connected to the image memory 40 through the data bus 42 in order to store data of an image obtained by the computation in the computer 34. The output buffer memory 44 has the same configuration as the image memory 40 and is synchronized with a clock from a timing controller 46 for its data readout operation. The data readout operation is executed according to an image scanning system of a display unit 48, such as a CRT, to which the output buffer memory 44 is connected through a D/A converter 50. Image data D from the output buffer memory 44 is converted to analog data by a D/A converter 50. A sync signal S7 from the timing controller 46 is combined or mixed with an image signal in the D/A converter 50, thereby producing a composite video signal S8, which is then supplied to the display unit 48. As a result, the reconstructed image of the object 14 is displayed on the display unit 48.

The processing unit 38 of the computer 34 has three main functions: control of the scan controller 18, transfer control of the hologram data, and image reconstruction process. The image reconstruction process corresponds to the step for executing the convolution using a kernel function.

As regards the function of the scan controller 18, after the data readout from the C-input and S-input buffer memories 30 and 32 is completed, the computer 34 instructs the scan controller 18 to emit an ultrasonic beam and also specifies which transducers will be driven. Under the control of the computer 34, the scan controller 18 allows the pulse generator 16 to drive the specified transducers.

The cos hologram data S5 and sin hologram data S6, resulting from the emission of one dose of ultrasonic beams to the object 14, are respectively stored in the input buffer memories 30 and 32 under the control of the computer 34. The computer 34 sequentially reads out these hologram data from the C-input and S-input buffer memories 30, 32 and transfers them to the image memory 40 through the data bus 42. The computer 34 then sequentially writes the data at the memory addresses of the image memory 40 which are determined in accordance with the location of the transducer that has emitted the ultrasonic beam and the depth of a to-be-detected area lying in the object 14.

After all of the transducers 12 in the ultrasonic probe 10 have been driven to emit the ultrasonic beams and all of the hologram signals resulting from the beam emission have been stored in the image memory 40, the image reconstruction process starts. In carrying out the image reconstruction process, first, hologram data is read out from the image memory 40 in the direction X (from the left to the right) and in the direction Z (from the top to the bottom) and supplied to the computer 34. The read out hologram data is single-lined data starting with the data stored in the memory address (0, 0) of the image memory 40. The single-lined cos and sin hologram data read out from the image memory 40 is converted into data which is in the form of a complex number according to equation (1) given below:

$$R_{CM}(x) = R_C(x) - jR_S(x) \qquad (1),$$

where x represents the location where the ultrasound is transmitted and received. The converted data is then quantized in a predetermined number of bits (e.g., 8 bits) or digitized.

With the basic case where a point reflector is the cause of an echo, the hologram data $R_{CM}(x)$ would be:

$$R_{CM}(x) = \exp[-j(Ax^2 + \phi)] \qquad (2),$$

where A and $\phi$ are given as follows:

$$A = 2\pi/\lambda z,$$

$$\phi = 4\pi z/\lambda, \qquad (3),$$

where $\lambda$ is the wave length of an ultrasonic beam, and z the distance between the point reflector and the vibrator. It should be noted that the reflection coefficient and the envelope of the ultrasonic beam are assumed to be "1" for simplicity.

To obtain a reconstructed image of the point reflector based on the synthetic aperture technique, the computer 34 performs a convolution using kernel function data, which has a smaller number of bits than the hologram data and is expressed as the following equation:

$$K(x) = \exp[jAx^2] \qquad (4),$$

and takes the absolute value of the resultant data of the convolution. Accordingly, the reconstructed image U(x) is expressed as follows:

$$U(x) = \left| \int_{-\infty}^{\infty} \{R_C(x) - jR_S(x)\} \exp[jA(X - x)^2] dx \right|. \qquad (5)$$

With the real part $K_C(x)$ and the imaging part $K_S(x)$, the kernel function K(x) in equation (5) is expressed as follows:

$$K(x) = K_C(x) + jK_S(x) \qquad (6).$$

Then, $$U(x) = \left| \int_{-\infty}^{\infty} \{R_C(x) - jR_S(x)\}\{K_C(X - x) + jK_S(X - x)\} dx \right|. \qquad (7)$$

This equation may be expressed as:

$$U(x) = \left| \int_{-\infty}^{\infty} R_C(x) K_C(X - x) dx + \int_{-\infty}^{\infty} R_S(x) K_S(X - x) dx + j \left( \int_{-\infty}^{\infty} R_C(x) K_S(X - x) dx - \int_{-\infty}^{\infty} R_S(x) K_C(X - x) dx \right) \right|. \qquad (8)$$

Actually, the hologram data is sampled in the X-direction, so that the integrations in equation (7) can be replaced with summations. Hence, $$U(x_j) = \left| \sum_i R_C(x_i) K_C(X_j - x_i) dx + \sum_i R_S(x_i) K_S(X_j - x_i) dx + j \left( \sum_i R_C(x_i) K_S(X_j - x_i) dx - \sum_i R_S(x_i) K_C(X_j - x_i) dx \right) \right|. \qquad (9)$$

From equation (9), it is obvious that the calculation of four types of convolution summations is necessary to obtain the reconstructed image, based on the synthetic aperture technique.

As described above, the kernel function data, which is prestored in the ROM 36 in the computer 34, corresponds to the hologram data according to the idea of the present invention and has a smaller number of bits than the hologram data, is read out and is subjected to addition and multiplication with the hologram data by the computer 34. For the fast calculation, this multiplication is carried out by using a conversion table that uses, as address data, the hologram data and the kernel function data, which is prestored in the memory of the computer 34. As explained above, the absolute value of the resultant data of the computation is taken and then stored in the output buffer memory 44. The aforementioned process of the computer 34 is repeated until the Z-address of the image memory 40 reaches "511." The stored data is read out and supplied to the display unit 48 to be displayed.

The aforementioned embodiment of the present invention can speed up the computation for obtaining a high-quality reconstructed image without impairing the resolution. The speeding up of the computation is based on the fact that the kernel function data is quantized or digitized and prestored in the ROM 36 of the computer 34 and further that the digital kernel function data has a smaller number of bits than the hologram signal.

Any multiplication in a digital processing is basically performed by repeating the addition of digital data. In general, therefore, the smaller the number of bits of the digital data, the shorter the time required for the multiplication and the simpler the arrangement of the hardware used for the computation. The speed of the aforementioned computation may also be increased by using a data table prestored in a memory of the computer 34, such as a ROM. In this case, when performing the convolution for image reconstruction, the smaller the number of bits of digital data, i.e., the kernel function data and the hologram data, the smaller the memory capacity for the data table can be. For example, to execute a multiplication of two 8-bit digital data, a memory capacity of $2^{16}$ words (64K words) is normally required for storing the table data. If one of the data is 4-bit data, the necessary memory capacity will be $2^{12}$ words (4K words). In other words, the memory capacity is reduced to quarter the memory capacity needed for two 8-bit data. Naturally, the computation speed for the image reconstruction can be increased by setting the number of bits of the kernel function data to be smaller than that of the hologram data. (According to conventional systems, the bit quantity of the kernel function data is normally set to be equal to or greater than that of the hologram data.) As the bit number of the kernel function data is decreased, the memory area in the computer 34 for the data table storage can also be reduced, accordingly. This reduces the time for accessing the memory, further increasing the speed of the computation for the image reconstruction.

In the aforementioned embodiment, the kernel function has been expressed as 4-bit binary data. The reduction in the bit number is normally considered to deteriorate the data accuracy, thus degrading the quality of a reconstructed image. In other words, it is normally considered that the speed-up of the data processing, by low bit-rate generation of the data, for the image reconstruction results in an undesirable deterioration of the quality of the reconstructed image. Contrary to this general assumption, however, the studies conducted by the present inventor show that even setting the bit number of the kernel function data smaller than that of the hologram data does not substantially impair the concerned image quality.

The efficiency of the image-signal processing apparatus according to the above-described embodiment may be evaluated by the change in the resolution and the amplitude of the side lobe of the reconstructed image, which results from the reduction of the bit quantity of the kernel function data. It is when the bit quantity of the kernel function data is set to 1 that the concerned image quality is degraded most. The following are the results of the evaluation in that particular case.

Figure 3A:
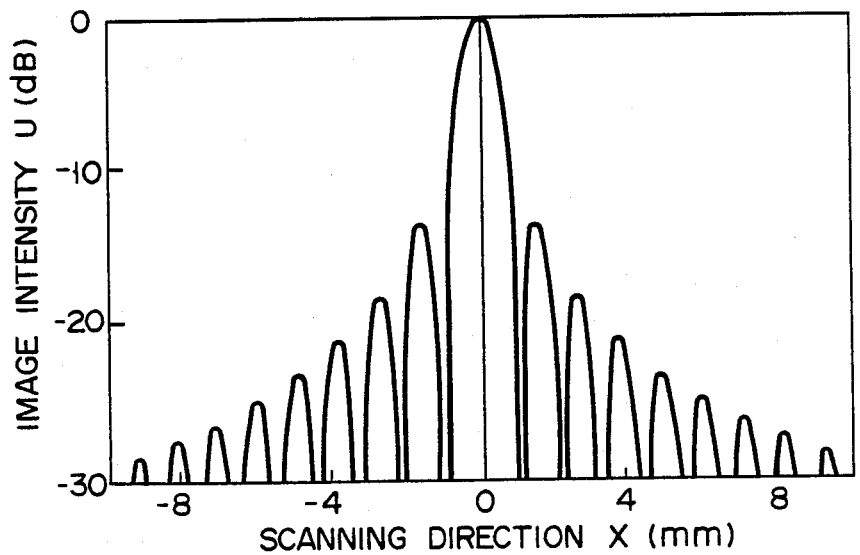
FIG. 3A is a graph illustrating a waveform of a reconstructed image of a point reflector obtained according to an ordinary arithmetic operation which uses an undigitized kernel function.

FIG. 3A illustrates the waveform of a reconstructed image according to a prior art which performs a convolution using an undigitized (i.e., unquantized) kernel function under the condition that the frequency of an ultrasonic beam is 3.5 MHz, the travelling speed of the ultrasound is 1,540 m/sec., the distance between the transducer 12 and the reflector of the object 14 is 75 mm, and the width of the ultrasonic beam at the reflector is 15 mm. FIG. 3B illustrates the waveform of a reconstructed image obtained under the same condition by executing the convolution with a 1-bit kernel function that is digitized according to the core concept of the present invention. As can be seen from FIG. 3A, with the convolution performed with the undigitized kernel function, the maximum amplitude of the side lobe of the reconstructed image is about $-13.3$ dB, while the resolution (which is defined as the main-lobe width at the amplitude of $-10$ dB) is 1.6 mm. In contrast, with the convolution performed with the digitized (1-bit) kernel function according to the present invention, the maximum side lobe level is about $-13.8$ dB and the resolution 1.7 mm. From this result, it is easily understood that the quality of the reconstructed image obtained with the 1-bit digital kernel function data is nearly equal to that resulting from the use of an undigitized kernel function. Contrary to the general concept that with N-bit hologram data used, the kernel function should be expressed as data of N bits or greater than N bits, the aforementioned comparison proves that even if the bit number of the kernel function is less than N or is 1 in the most extreme case, a reconstructed image can be obtained with substantially the same quality as that attained by the conventional technique. In view of the above, the present invention can increase the speed of the computation for image reconstruction while the quality of the reconstructed image is kept at a high level.

An ultrasonic computed tomography system including an image-signal processing apparatus according to a second embodiment of the present invention will now be described with reference to FIG. 4. FIG. 4 uses the same reference numerals for the parts similar to those shown in FIG. 1.

A computer 60 includes a ROM 62, which prestores a kernel function data quantized (digitized) to have an n-th order (n: a positive integer). The kernel function stored in the ROM 62 is quantized in such a way the values of quantized levels are represented as a series of $\pm 2^{-k}$, where $k \leq n$, $k = 0, 1, 2, \ldots n$. (Zero may be included in the series.) For example, with n being 2, the quantized levels are:

$$-\frac{1}{2^0}, -\frac{1}{2^1}, -\frac{1}{2^2}, 0, \frac{1}{2^2}, \frac{1}{2^1}, \frac{1}{2^0}.$$

It should be noted that the quantized kernel function may be encoded before it is stored in the ROM 62.

The convolution peformed with hologram data and the kernel function quantized in the aforementioned manner can produce a high-quality reconstructed image of an object with a higher speed. This is because the quantization of the kernel function into the series simplifies the multiplication of the kernel function and the hologram data.

According to the embodiment shown in FIG. 4, the multiplications can be simplified by the flowing procedures:

(1) When the sign of the value of the kernel function is negative, the sign of the hologram data is inverted.
(2) When the kernel function value is "0," the computation result is set to be zero.
(3) When the absolute value of the kernel function value is "¼," the hologram data is shifted to the right by two bits (i.e., the hologram data is reduced to a quarter).
(4) When the absolute value of the kernel function value is "½," the hologram data is shifted to the right by one bit (i.e., the hologram data is halved).
(5) When the absolute value of the kernel function value is "1," the hologram data is not bit-shifted.

As is exemplified above, such data quantization enables the multiplications of the kernel function and the hologram data to be replaced by operations such as the sign inversion, setting the resultant data to 0 and the data shifting. Naturally, this can significantly speed up the computation.

Even the use of the technique hardly deteriorates the quality of a reconstructed image for the following reason. The worst case would be when n=0 and the kernel function does not contain "0," i.e., when the kernel function data is expressed by the values "$-1$" and "1." But, this case corresponds to the one where the number of bits is "1" in the first embodiment. It has already been explained that such a case will provide a sufficient quality of the reconstructed image.

In other words, when the quantized kernel function has a series of values "$-1$," "$-0.5$," "$-0.25$," "0," "0.25," "0.5," "1," the computation for the image reconstruction can be performed easily and at a higher speed by properly using the aforementioned procedures.

With the use of the kernel function expressed in the aforementioned fashion, the convolution of the kernel function and the hologram data can be simplified by a bit shifting and sign inversion of the hologram data. This significantly shortens the time required for a complicated computation for the synthetic aperture process and considerably contributes to speeding up the image reconstruction process.

Although the present invention has been shown and described with reference to particular embodiments, various changes and modification which are obvious to a person skilled in the art to which the invention pertains are deemed to lie within the spirit and scope of the invention.

It is also effective to use the kernel function multiplied by $2^m$ (m: integer). This modification apparently requires an additional multiplication associated with the term $2^m$; however, it can be executed by shifting the hologram data to the left by m bits when $m>0$ or to the right by m bits when $m<0$, thus assuring a higher computation for image reconstruction.

It is understood that because the use of such kernel data simply increases the amplitude of the reconstructed image by $2^m$, the modification provides a similar quality of a reconstructed image.

What is claimed is:

1. An apparatus for reconstructing an image signal of an object on the basis of a synthetic aperture technique, said apparatus comprising:
    (a) transducer means for emitting a radiation to the object and for detecting the corresponding radiation reflected from the object to convert the reflected radiation into an electrical signal;
    (b) hologram generator means, connected to said transducer means, for generating hologram data representing at least one hologram signal in response to said electrical signal and for digitizing said hologram data to have a predetermined first number of bits; and
    (c) computer means, connected to said hologram generator means, for receiving said digital hologram data to perform a predetermined arithmetic operation including additions and multiplications, based on the syntheitc aperture technique, on said digital hologram data and digital kernel function data, thereby producing a reconstructed image signal of the object, said digital kernal function data being quantized to have a second number of bits smaller than the first number of bits and have the absolute value of $2^m \cdot 2^{-k}$, where "m" is zero or an integer and "k" is a positive integer, whereby the number of times the muliplications included in said arithmetic operation are replaced by inversion of the sign of said hologram data is increased to speed up the performance of said arithmetic operation for image reconstruction.

2. The apparatus according to claim 1, wherein said computer means comprises:
    memory means for prestoring said digital kernel function data quantized to have an n-th order (n: a positive integer) in such a manner that values of quantized levels are represented as a series of $\pm 2^{-k}$, where $k \leq n$, $k=0, 1, 2 \ldots n$.

3. The apparatus according to claim 2, wherein said digital kernel function data is quantizied to include zero in the values of quantized levels.

4. The apparatus according to claim 2, wherein said computer means performs the arithmetic operation on said digital hologram data and digital kernel function data in such a manner that the number of times the muliplications included in said arithmetic operation are replaced by inversion of the sign of said hologram data and bit-shifting of said hologram data is increased.

5. The apparatus according to claim 2, wherein said memory means includes read only memory means for prestoring said kernel function data whose bit number is set to be the extent of at least half the bit number of said hologram data.

6. The apparatus according to claim 2, wherein said read only memory means prestores said kernel function data which is quantized so as to have values of "−1," "−0.5," "−0.25," "0," "0.25," "0.5" and "1," and wherein said computer means replaces said multiplications included in said convolution with an inversion of the sign of said hologram data when said value of said kernel function data is "−1" and with a process for setting the multiplication result to zero irrespective of the value of said hologram data when said value of said kernel function data is "0," thereby shortening the time required for image reconstruction.

* * * * *